(12) United States Patent
Lancial

(10) Patent No.: US 7,744,630 B2
(45) Date of Patent: Jun. 29, 2010

(54) FACET REPAIR AND STABILIZATION

(75) Inventor: Mike E. Lancial, St. Louis Park, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 571 days.

(21) Appl. No.: 11/274,385

(22) Filed: Nov. 15, 2005

(65) Prior Publication Data

US 2007/0112428 A1    May 17, 2007

(51) Int. Cl.
*A61B 17/70* (2006.01)
(52) U.S. Cl. .................. 606/247; 606/246; 606/249; 623/17.12
(58) Field of Classification Search ............. 606/313, 606/247, 246, 248, 249, 279, 280–299, 70, 606/71; 623/17.11, 17.12, 17.13, 17.14, 623/17.15, 17.16
See application file for complete search history.

(56) References Cited

U.S. PATENT DOCUMENTS

| | | | |
|---|---|---|---|
| 3,875,595 A * | 4/1975 | Froning | 623/17.12 |
| 4,743,260 A | 5/1988 | Burton | |
| 5,002,576 A * | 3/1991 | Fuhrmann et al. | 623/17.15 |
| 5,375,823 A | 12/1994 | Navas | |
| 5,540,688 A | 7/1996 | Navas | |
| 5,549,679 A * | 8/1996 | Kuslich | 623/17.12 |
| 5,888,220 A | 3/1999 | Felt et al. | |
| 6,187,048 B1 | 2/2001 | Milner et al. | |
| 6,235,059 B1 * | 5/2001 | Benezech et al. | 623/17.16 |
| 6,565,605 B2 | 5/2003 | Goble et al. | |
| 6,579,319 B2 | 6/2003 | Goble et al. | |
| 6,595,998 B2 * | 7/2003 | Johnson et al. | 606/90 |
| 6,610,091 B1 | 8/2003 | Reiley | |
| 6,635,087 B2 * | 10/2003 | Angelucci et al. | 623/17.11 |
| 6,645,248 B2 * | 11/2003 | Casutt | 623/17.12 |

(Continued)

FOREIGN PATENT DOCUMENTS

DE    10135771 A1 *  2/2003

(Continued)

OTHER PUBLICATIONS

European Patent Office, International Search Report and Written Opinion in corresponding PCT application PCT/US2006/043736, dated Mar. 15, 2007, 11 pgs.

*Primary Examiner*—Eduardo C Robert
*Assistant Examiner*—Jan Christopher Merene
(74) *Attorney, Agent, or Firm*—Crompton, Seager & Tufte, LLC

(57) ABSTRACT

An implant for use with the opposing facets of two adjacent vertebrae includes a facet bearing body having a cavity for receiving a filler material, and at least one fixation wing for securing the facet bearing body to at least one of the two vertebrae, wherein the facet bearing body is positionable between the opposing facets and the at least one fixation wing is fixable to at least one of the two vertebrae. The filler material may be an in situ curable polymer such as bone cement, a polyurethane or an elastomer. To stabilize the adjacent vertebrae, the facet bearing body is inserted between the opposing facets of the adjacent vertebrae. The at least one fixation wing is fixed to at least one of the two adjacent vertebrae. The filler material is injected into the cavity and allowed to harden.

20 Claims, 7 Drawing Sheets

U.S. PATENT DOCUMENTS

| | | |
|---|---|---|
| 6,652,587 B2 | 11/2003 | Felt et al. |
| 6,837,905 B1 * | 1/2005 | Lieberman ............... 623/17.16 |
| 7,001,431 B2 * | 2/2006 | Bao et al. ................. 623/17.12 |
| 2001/0027319 A1 | 10/2001 | Ferree |
| 2002/0133155 A1 | 9/2002 | Ferree |
| 2003/0125738 A1 * | 7/2003 | Khanna ....................... 606/61 |
| 2003/0220649 A1 | 11/2003 | Bao et al. |
| 2004/0006343 A1 * | 1/2004 | Sevrain ....................... 606/61 |
| 2004/0059417 A1 * | 3/2004 | Smith et al. .............. 623/17.11 |
| 2005/0124993 A1 * | 6/2005 | Chappuis .................... 606/61 |
| 2005/0197702 A1 * | 9/2005 | Coppes et al. ........... 623/17.12 |
| 2006/0246105 A1 * | 11/2006 | Molz et al. .................. 424/423 |
| 2007/0135814 A1 | 6/2007 | Farris |

FOREIGN PATENT DOCUMENTS

| | | | |
|---|---|---|---|
| EP | 0 669 109 B1 | 8/1995 | |
| WO | WO 94/17745 | 8/1994 | |
| WO | 0265954 A1 | 8/2002 | |
| WO | WO/2004/016205 * | 2/2004 | ............. 623/17.12 |
| WO | 2006130791 A1 | 12/2006 | |
| WO | 2007/070785 A1 | 6/2007 | |

* cited by examiner

FACET REPAIR AND STABILIZATION

TECHNICAL FIELD

The present invention is related to spinal stabilization devices. More particularly, the present invention relates to devices and systems for addressing back pain originating in the vertebrae by adding devices for the flexible stabilization of the facet joints and adjacent spinous processes.

BACKGROUND

The spinal column is a highly complex system of bones and connective tissues that provides support for the body and protects the delicate spinal flexible connecting member and nerves. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal flexible connecting member and nerves is located behind the vertebral bodies.

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers may be referred to as intervertebral discs. These more than 20 bones are anatomically categorized as being members of one of four classifications: cervical, thoracic, lumbar, or sacral. The cervical portion of the spine, which comprises the top of the spine up to the base of the skull, includes the first 7 vertebrae. The intermediate 12 bones are the thoracic vertebrae and connect to the lower spine comprising the 5 lumbar vertebrae. The base of the spine is the sacral bone (including the coccyx). The component bones of the cervical spine are generally smaller than those of the thoracic and lumbar spine. In spite of these complexities, the spine is a highly flexible structure capable of a high degree of curvature and twist in nearly every direction.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal pathologies may threaten the critical elements of the nervous system housed within the spinal column.

A variety of systems and surgical procedures have been disclosed in the art to alleviate the symptoms of these and other spinal pathologies. One of the most common surgical procedures today is arthrodesis, or spine fusion, of one or more spine segments. Spine fusion is used to treat many spinal disorders, including kyphosis, spondylolisthesis, and lordosis. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Also, the fusion device, whether artificial or biological, may migrate out of the fusion site.

Instead of fusing sections of the spine, various different devices have been implanted into the spine to stabilize the spine without completely restricting movement. These flexible spinal stabilization methods may not result in complete spinal fusion. Some systems include implanting artificial assemblies in or on the spinal column. These assemblies may be classified as anterior, posterior, or lateral implants. As the classifications suggest, lateral and anterior assemblies are coupled to the anterior portion of the spine that is the sequence of vertebral bodies. Posterior implants generally comprise pairs of rods that are aligned along the axis of the bones and which are attached to the spinal column by hooks coupled to the lamina or to the transverse processes. Implants may also be attached by screws or attachment members inserted through the pedicles.

One posterior stabilization method includes spinal immobilization utilizing pedicle screws and wire. Other spinal systems may include a variety of other procedures and apparatuses for attending spinal problems and pain. However, there is a continual need for alternative systems and devices for stabilization of the spine.

SUMMARY

In one embodiment, the present invention is an implant for use with the opposing facets of two adjacent vertebrae. The implant includes a facet bearing body, a cavity in the facet bearing body, and a pair of opposing fixation wings for securing the implant to the adjacent vertebrae. The facet bearing body is inserted into the facet joint between the two adjacent vertebrae and the fixation wings are fixed to the vertebrae to fix the implant in position. A filler material is injected into the cavity to inflate the facet bearing body so as to support and space apart the vertebrae. The filler material may be an in situ curable polymer.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
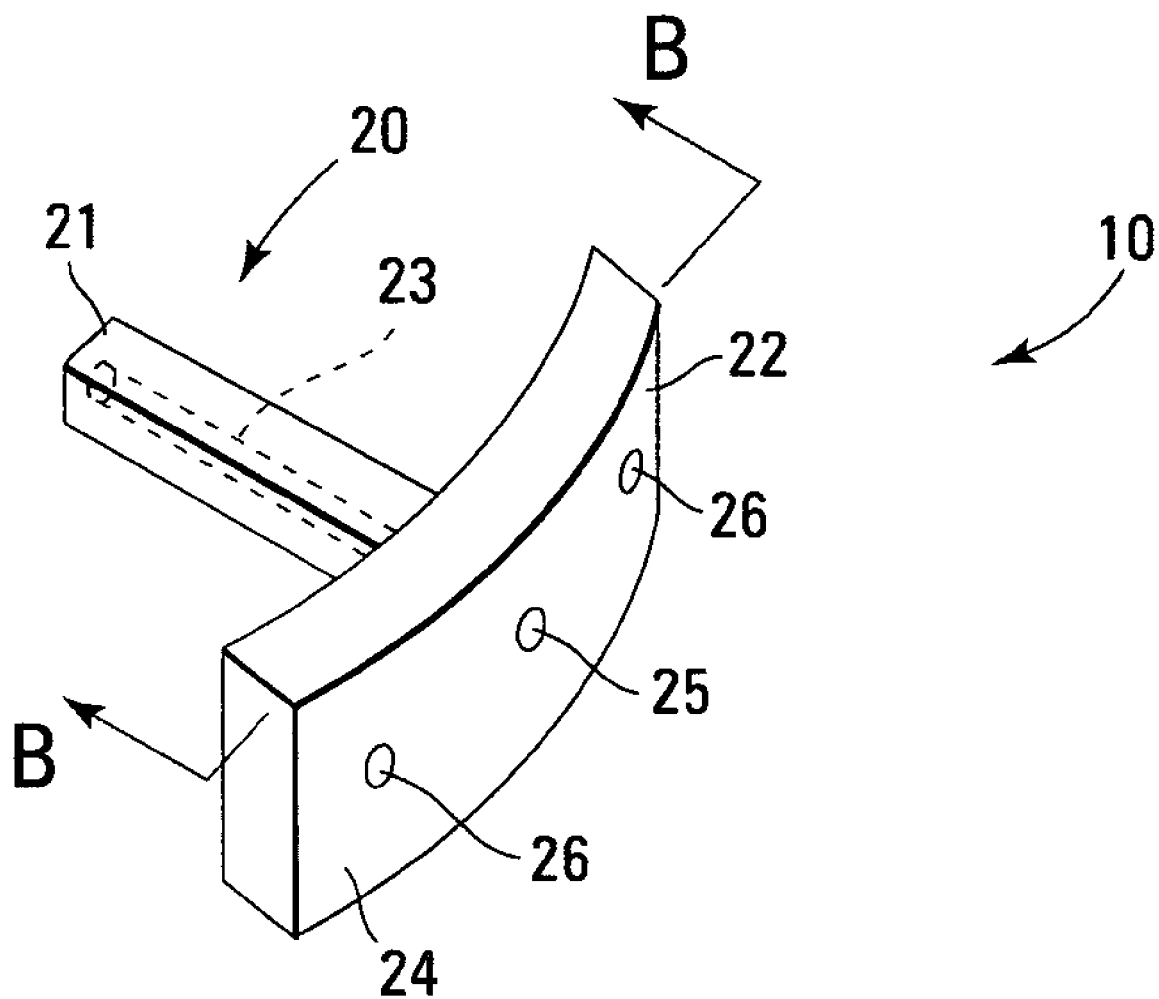
FIG. 1 shows a perspective view of an implant according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present invention includes multiple apparatuses and methods for spinal stabilization. The use of the term "stabilization" in the present description refers to securing adjacent vertebrae such that the movement between them is limited to a desired amount. Stabilization may also be achieved by not reducing movement but by simply providing increased structural integrity between adjacent vertebrae.

Figure 2:
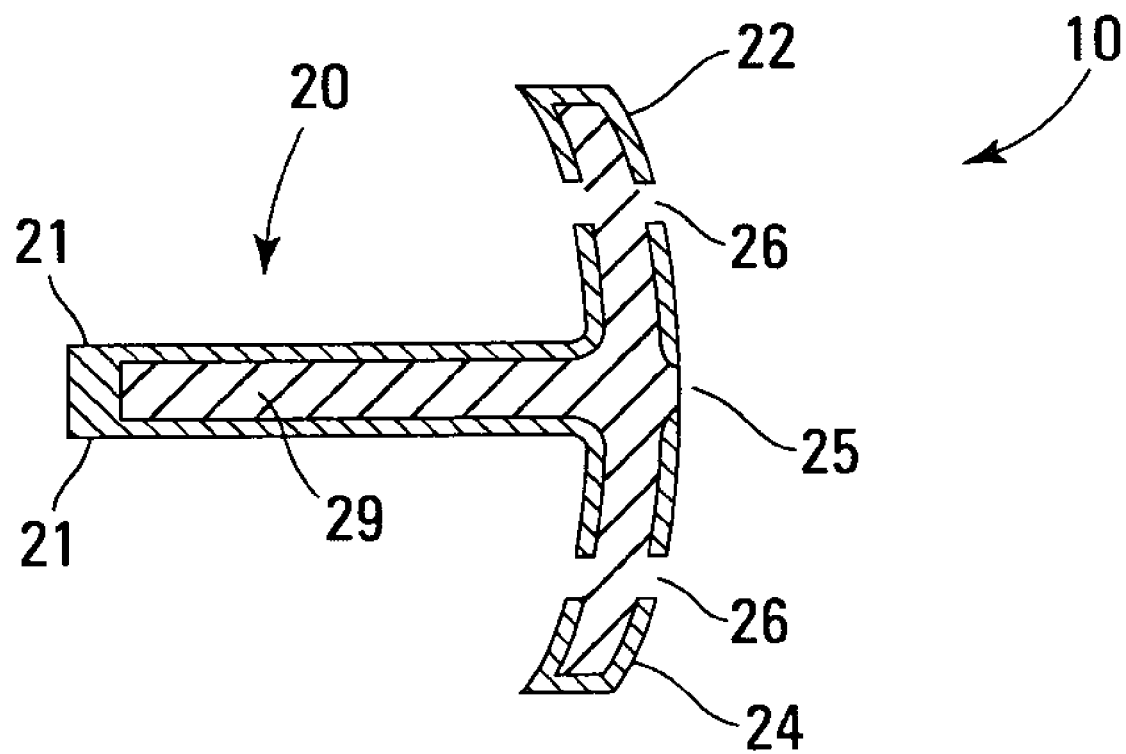
FIG. 2 shows a cross-sectional view of the implant of FIG. 1 taken along lines B-B.

A facet implant 10 according to one embodiment of the present invention is illustrated in FIGS. 1 and 2. The facet implant 10 is a prosthesis for the augmentation, stabilization, and/or replacement of a diseased, traumatized, or otherwise compromised facet of a mammalian vertebra. The facet implant 10 may provide joint spacing, joint stabilization, joint capsule replacement, cushioning and/or an articulating surface for an opposing pair of facets to a facet joint. One embodiment of the facet implant 10 may include a bearing body 20 (a facet bearing body) having a facet bearing surface 21, a first fixation wing 22, and a second fixation wing 24. The bearing body 20 may also be known as an articulating body or a facet bearing means. Likewise, the facet bearing surface 21 may also be known as an articulating surface and the fixation wings 22 and 24 may be known as fixation means or fixation tabs. Other terms may also be utilized to describe these portions of the facet implant 10 without changing the nature of the invention.

The bearing body 20 of the facet implant 10 may be attached to or integrally formed with the fixation wings 22 and 24 such that the bearing body 20 extends in a generally perpendicular direction from the plane created by the fixation wings 22 and 24. The fixation wings 22 and 24 may further include holes 26 to receive means for attaching the facet implant 10 to the spine in the desired position. The fixation wings 22 and 24 may be rigidly attached to the bearing body 20. However, in alternative embodiments, the bearing body 20 and fixation wings 22 and 24 may be attached to the vertebrae in a deformable manner such that the bearing body 20 and/or fixation wings 22 and 24 can be bent, twisted, formed, shaped, or generally positioned relative to each other and/or relative to the vertebrae. The bearing body 20 and fixation wings 22 and 24 can themselves be deformable as well. Moreover, the bearing body 20 and fixation wings 22 and 24 can be made of one piece or more than one piece of material, including, but not limited to, materials that are layered, woven, stitched, or otherwise joined with other materials. The facet bearing surface 21 is present on each side of bearing body 20.

Implant 10 may have other shapes and configurations. Exemplary configurations are shown and described in U.S. patent application Ser. No. 11/221,938 entitled "Facet Replacement/Spacing and Flexible Spinal Stabilization", filed Sep. 8, 2005, which is hereby incorporated by reference herein in its entirety.

A cavity 23 is formed in the bearing body 20 and is accessible via an opening 25. The cavity 23 is adapted to receive a filler material 29. In one embodiment, the facet bearing body 20 is adapted to expand from a first or collapsed configuration to a second or expanded configuration upon the placement of a filler material 29 in the cavity 23. In the first, collapsed configuration the bearing body 20 has a reduced or lowered profile to facilitate a minimally-invasive implantation procedure. The bearing body 20 may thus be inserted into a space between adjacent vertebrae without requiring significant distraction and resection of any residual material between the vertebrae.

The second configuration may be a maximum size or reflect the greatest amount of expansion permitted by the implant 10. In other embodiments, however, the second configuration may be an intermediate configuration or smaller than the maximum amount of expansion permitted by the implant 10. The amount of filler material 29 placed into the cavity 23 may be determined according to the patient's needs or surgical goals.

In one embodiment, the facet implant 10, bearing body 20, and the fixation wings 22 and 24 may be made of a polymeric elastomer material. In further embodiments, the facet bearing body 20 and the fixation wings 22 and 24 may be made of other materials, such as, but not limited to, polyurethane, fluoropolymers, polyetheretherketone, ultra-polyetheretherketone, polycarbonate based polyurethane elastomer, etc. The bearing body 20 and bearing surface 21 may be preferably made of a polymer material that mimics the body's natural facet joints, such as ultra high molecular weight polyethylene or some other polymer. The polymer selected may be self-lubricating, low friction, abrasion resistant, and biocompatible. The polymer selected may also include certain lubricious properties.

The bearing body 20 and fixation wings 22 and 24 may be made entirely of a desired elastomer material or may include a combination of materials that may be integrated in any manner desired to achieve a desired result. Desired results may include different structural characteristics and/or different surface characteristics. Additional embodiments may include a first core material coated by a second surface material.

In one embodiment, all or a portion of the facet implant 10 is formed of a textile material. Textile fabrication processes for making a textile material include two- and three-dimensional variations of braiding, knitting and weaving. One exemplary three-dimensional weave pattern is known as a honeycomb weave. A honeycomb weave has a three-dimensional, cell-like structure in which long floats form the periphery of each cell. The interlacing is progressively tightened, towards the cell centers, with the tightest interlacing occurring at the center of the cell. This weave pattern creates a structure of hollow pickets between raised portions, similar to a waffle. The face and back of such a woven textile or fabric are similar, with the midpoint on the cell on one side serving as the outer corner on the other side. In other words, the high point on one side of the textile or fabric is the low point on the other side. An exemplary honeycomb weave pattern is available at Offray Speciality Narrow Fabrics, Inc., of Chester, N.J.

A honeycomb weave provides a cell structure having a substantially completely interconnected porosity in three dimensions throughout the fabric. Such porosity permits the ingrowth of bone material and transfer of fluids. For example, bone material may migrate and fluids may transfer into and out of the cavity 23 through the fabric of the facet implant 10 while the facet implant 10 restrains extrusion and/or migration of the filler material 29. A porous or open construction to the facet implant 10 may also be provided according to other means of braiding, weaving and knitting and are also contemplated by the present invention.

Making the facet implant 10 with substantially flexible materials may allow for the joints to move freely after implantation. Making the facet implant 10 with stiffer materials may restrict the movement of the opposing facets. In other words, using materials with a high modulus of elasticity or a low modulus of elasticity may change the amount the spine is restricted from moving. One such modulus range may be from approximately 0.5 megapascals to 3 megapascals. Depending on the needs for each insertion, a variety of material and material combinations may be incorporated into the implant 10.

In one embodiment, the bearing body 20 is a balloon having non-compliant or shape restricted characteristics. For example, particular regions of the implant 10 may be more or less compliant or able to stretch than others, or the implant 10 may be more or less compliant or able to stretch along particular axes or planes than others. In this manner, the shape of the bearing body 20 in the second configuration may be predetermined or at least predicted and may be chosen to restrict or direct the amount of expansion or extension in particular directions or planes. Non-compliant or shape restricted characteristics may be imparted to the implant 10 by adjusting the thickness of the walls of the implant 10 or by incorporating materials that have a chosen degree of elasticity.

Figure 3:
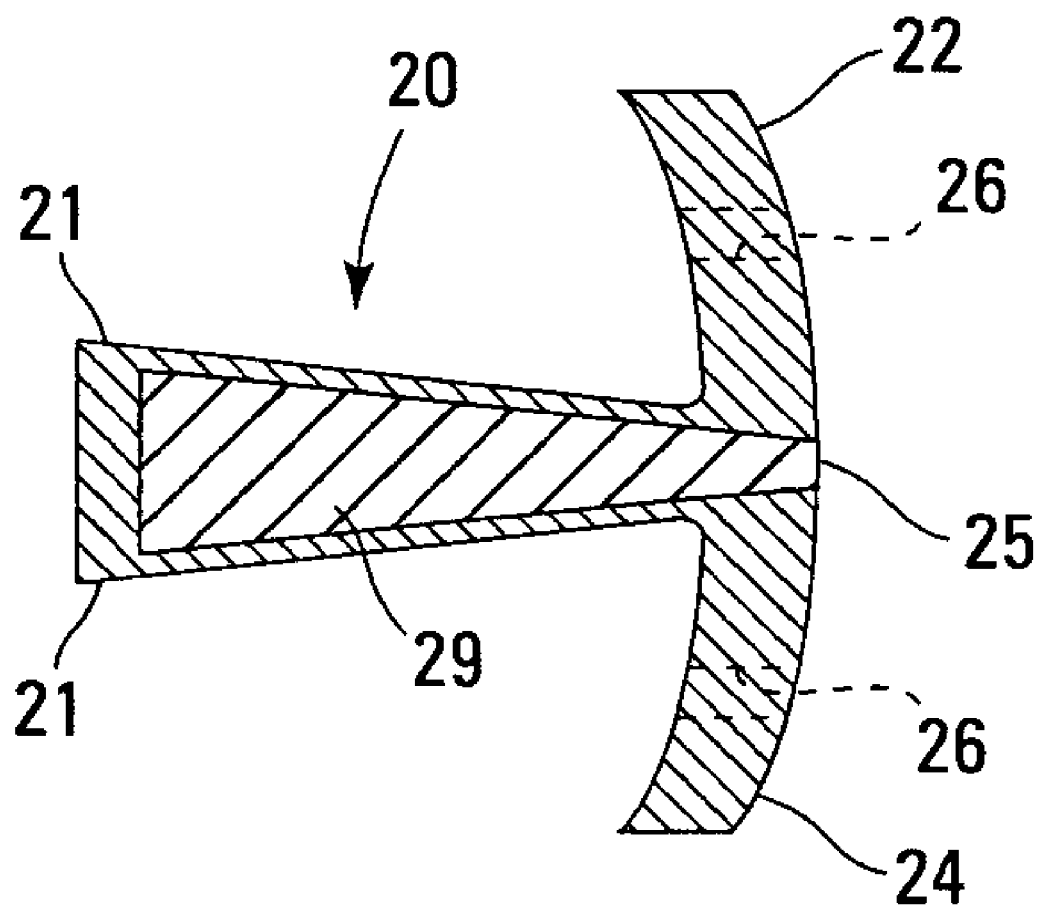
FIG. 3 shows a cross-sectional view of an implant according to another embodiment of the present invention.

In one embodiment, as is shown in FIG. 2, the cavity 23 extends into the fixation wings 22 and 24. In this embodiment, the entire implant 10 may be formed of a non-compliant or shape restricted balloon. In other embodiments, as is shown in FIG. 3, the cavity 23 is disposed solely within the facet bearing body 20 or within a portion of the facet bearing body 20.

Figure 4:
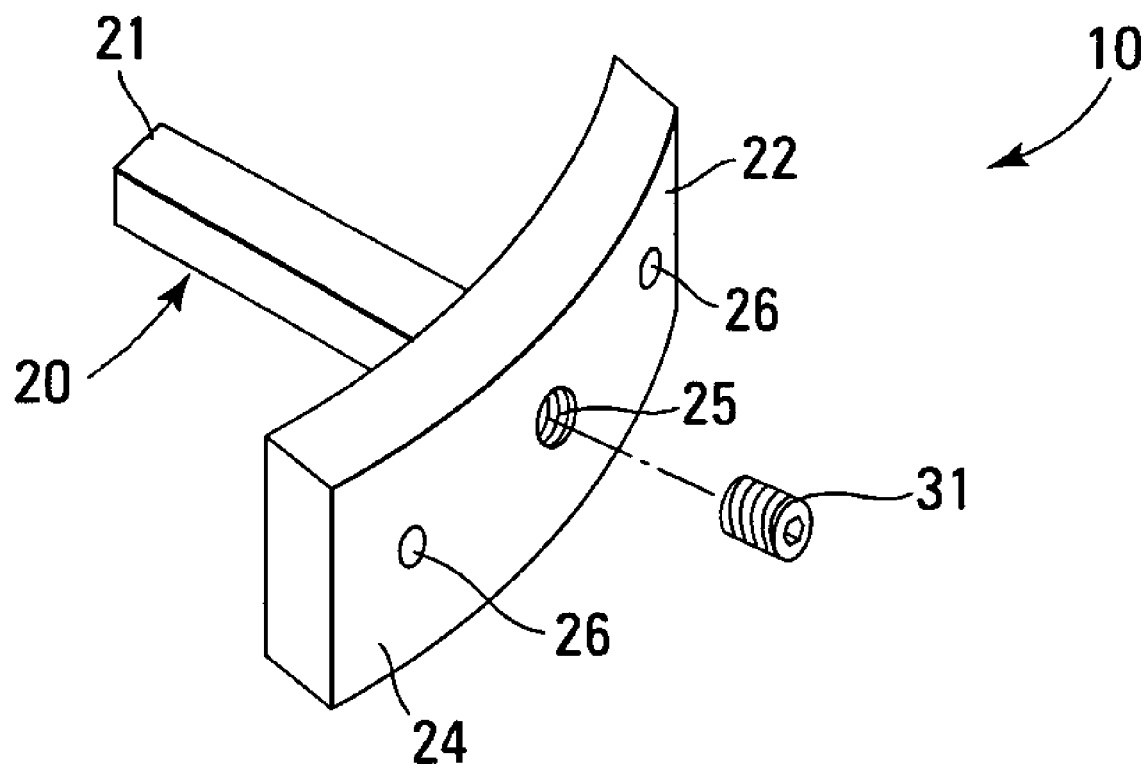
FIG. 4 shows a cross-sectional view of an implant according to another embodiment of the present invention.

The opening 25 may be provided with a means for sealing the cavity 23 after injection of the filler material 29. In one embodiment, as shown in FIG. 4, the implant 10 includes a threaded member 31 threadedly engageable to the opening 25. When the threaded member 31 is inserted into the opening 25, the opening is sealed to prevent leakage of the filler material 29. In other embodiments, the implant may include a biocompatible adhesive or patch placed over the opening 25. In other embodiments, the opening 25 is self-sealing. For example, the opening 25 may be covered with a material that is capable of being pierced and re-sealing. Alternately, the opening 25 may be covered with a fabric material having a weave through which the filler material 29 may be injected without compromising the fabric.

The filler material 29 may be made of various materials. In one embodiment, the filler material 29 may be a liquid or at least sufficiently flowable to permit the filler material 29 to be injected into the cavity 23. In one embodiment, the filler material 29 is made of a curable or a hardenable material. The filler material 29 may be injected into the cavity 23 in a fluid or flowable state and thereafter cure or harden into a more rigid state. The filler material 29 may be chosen so that after curing or hardening the filler material 29 is a gel-like, semi-rigid or rigid material. Thus, after curing or hardening, the filler material 29 may still retain a degree of flexibility, elasticity or flowability. The bearing body 20 may thus provide a degree of shock absorption or cushioning to the vertebrae. A hardenable or curable filler material 29 may seal the opening 25 upon hardening or curing such that a means for sealing the opening 25 is not necessary.

In one embodiment, the filler material 29 is an in situ curable polymer. Exemplary in situ curable polymers include bone cement, polyurethanes or other in situ curable elastomers or polymers. In one embodiment, the filler material 29 is adapted to facilitate or encourage bone growth.

The filler material 29 may be chosen to be self-hardening or self-curable, or hardenable or curable upon the application of heat, light, air, a curing agent or other hardening or curing means. The filler material 29 may be chosen to harden or cure shortly after injection into the cavity 23 or over the next few hours or days. Once the filler material 29 has hardened or cured, the implant 10 may function as a load bearing member and may serve to retain the vertebrae in a spaced relationship to one another, as well as to support and stabilize the adjacent vertebrae.

Figure 5:
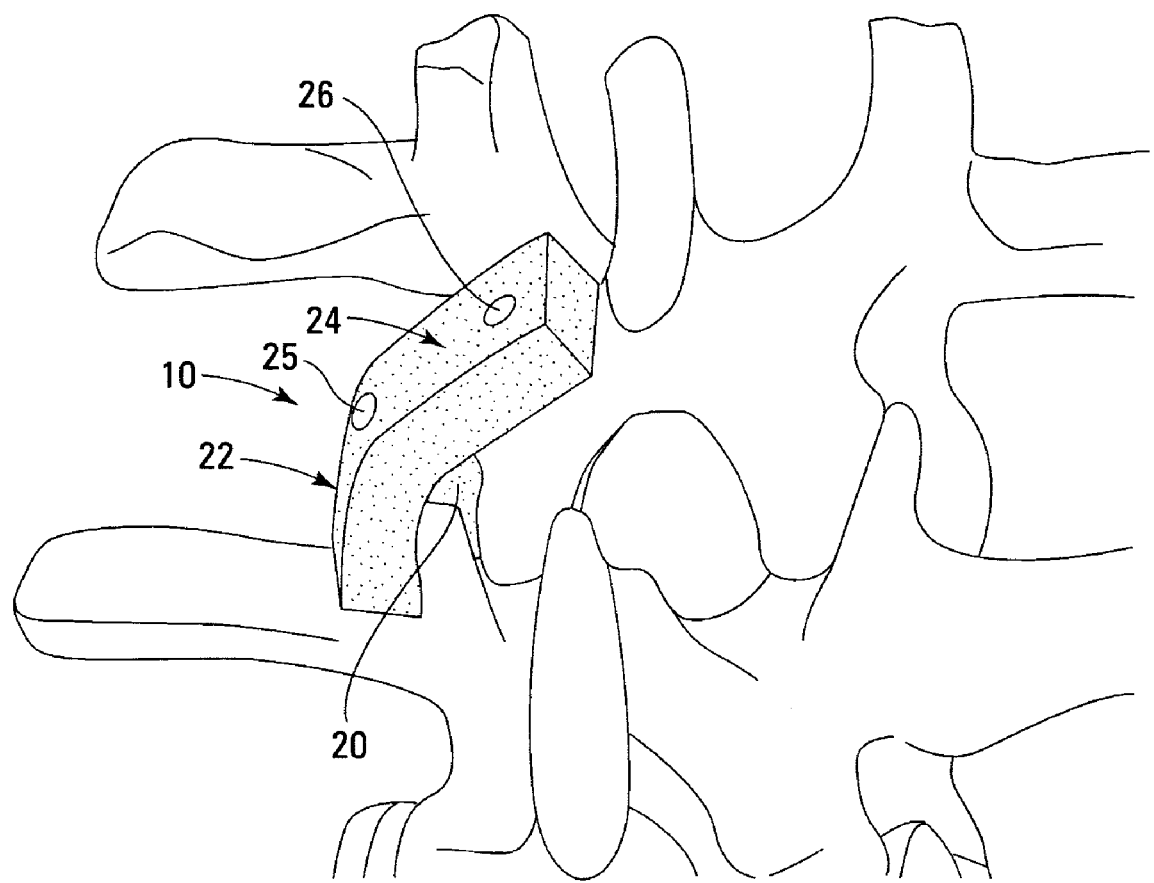
FIG. 5 shows the implant of FIG. 1 inserted onto the spine.

FIG. 5 shows the implant 10 inserted onto the spine. In order to more precisely fit the implant 10 to the patient's anatomy, the facet joint may be measure or sized prior to inserting the implant 10. After measuring or sizing, a custom made implant 10 may be constructed, or the closest sized implant 10 of a set may be chosen for implantation. In one embodiment, the facet joint is sized radiographically. Radiographic sizing or sizing according to any other means may be performed either before or after the facet surfaces are resected or resurfaced.

The facet implant 10 may be inserted by first opening a surgical site around the facet joint in any manner desired. The lateral joint capsule may then be cut. The medial side of the capsule also may be cut to eliminate a possible pain source. Alternatively, the lateral and medial capsule may be left intact to provide improved stability. The faces of the facet joints to be stabilized may then be resected a desired amount. In some embodiments, and depending on the particular shape of the facet implant 10, the facets may not be resected at all.

Figure 6A:
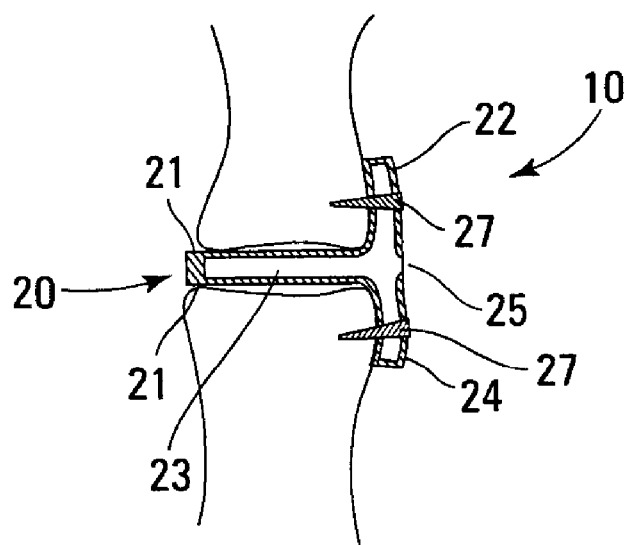
FIG. 6A shows the implant of FIG. 1 inserted between adjacent vertebrae while in a collapsed configuration.
Figure 6B:
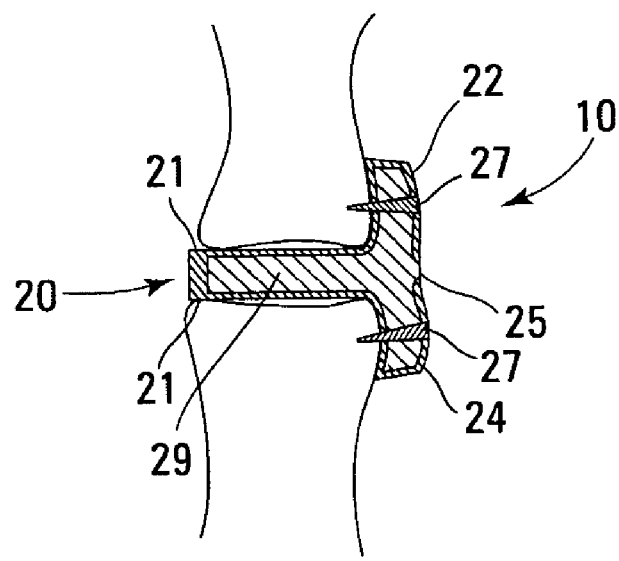
FIG. 6B shows the implant of FIG. 6A in an expanded configuration.

The bearing body 20 with the facet bearing surface 21 may then be inserted between the opposing faces of the facet joint. As illustrated in FIGS. 6A and 6B, one insertion position may include positioning the fixation wings 22 and 24 on the superior and inferior vertebrae with the bearing body 20 secured between the opposing facets. Finally, the facet implant 10 is secured in place by attaching the fixation wings 22 and 24 to the vertebrae utilizing one or more attachment members 27 or other fixation means.

Each hole 26 may accept or engage an attachment member 27 for attaching the implant 10 to the spine (See FIG. 6A). Each hole 26 may be replaced with other attachment member engaging means complementary to the attachment members 27 as needed. Attachment members 27 may be any type of appropriate biomedical attachment member 27 or may be replaced with any type of bone attachment anchors, screws, bone fasteners, bone attachment means, or any other fixation means for attaching the facet implant 10 to the spine in the desired position. When the attachment member 27 is a screw, for example, the screw type and length may be selected depending on the screw's insertion point. Moreover, the angle of insertion of the attachment members 27 may be selected to accommodate the desired attachment member 27. In still further embodiments, the facet implant 10 may also be secured to the bone surface using a biomedical adhesive in addition to, or in alternative to, attachment member 27. Another fixation means may include a post cemented into a cavity created in the bone. Such an implant may be similar to a dental post or a hip stem.

The attachment member 27 for the superior vertebra may be targeted to go through the resected bone surface, i.e., the remaining portion of the facet, and into the lamina. The attachment member 27 for the inferior vertebra may go through some portion of resected bone surface and into the pedicle. As may be appreciated, depending on the size of the implant 10, the size of the fixation wings 22 and 24, the amount of resected bone, and the length of the attachment members 27, a variety of facet implant 10 positions and attachment member 27 paths may be selected by one of skill in the art to achieve the intended results. Moreover, as discussed further herein, various alternative embodiments of the facet implant 10 may be more useful depending on the amount of the facet joint removed during the insertion process. The bearing body 20 and the facet bearing surface 21 of the facet implant 10 may provide spacing, cushioning, support, and/or an articulating surface to the opposing facets of the facet joint. The fixation wings 22 and 24 may be bent and deformed to adapt to the contours of each vertebra and to insure the correct positioning of the bearing body 20. Greater or lesser amounts of force may be exerted on the vertebrae depending on the desired results.

The fixation wings 22 and 24 of facet implant 10 may be bent, stretched, or otherwise deformed from their initially planar orientation to conform to each vertebra. The fixation wings 22 and 24 help to stabilize the relative positions of the opposing facet surfaces around the bearing body 20 by exerting a restraining force on the vertebrae. The restraining force may hold the facet surfaces in a desired orientation and may prevent the facet joint from moving out of a desired orientation. The force exerted by the fixation wings 22 and 24 on the two successive vertebrae depend on the material utilized to construct the facet implant 10 and how and where the fixation wings 22 and 24 are secured to the bone. The "T" shaped structure of the facet implant 10 may be twisted and stretched as desired in order to exert force in the desired manner to achieve the desired stabilization. For example, the fixation wings 22 and 24 may be "stretched" out before being secured, resulting in an increased restraining or compressive force acting on the facet joint and facet surfaces. Insertion of the facet implant 10 and the final position of the facet implant 10 may therefore be highly customizable. In alternative embodiments, one or two or more fixation wings may be utilized to form the facet implant 10 such that it is not necessarily T-shaped.

After the fixation wings 22 and 24 are affixed to the vertebrae, the filler material 29 may be injected into the cavity 23. The filler material 29 may be injected into the cavity 23 with an injection tool such as a hollow needle or syringe or any other suitable means for injecting the filler material 29 into the cavity 23.

In one embodiment, a sufficient quantity of filler material 29 is injected into the cavity 23 to cause the bearing body 20 to expand along an axis of the spine. For example, FIG. 6A shows the facet bearing body 20 having a first dimension along a longitudinal axis of the spine. After injection of the filler material 29 into the cavity 23, as is shown in FIG. 6B, the facet bearing body 20 has a second, greater dimension along the axis of the spine. The size of the cavity 23 and the amount of filler material 29 injected may be chosen to support the adjacent vertebrae in a spaced relationship to one another.

Figure 7A:
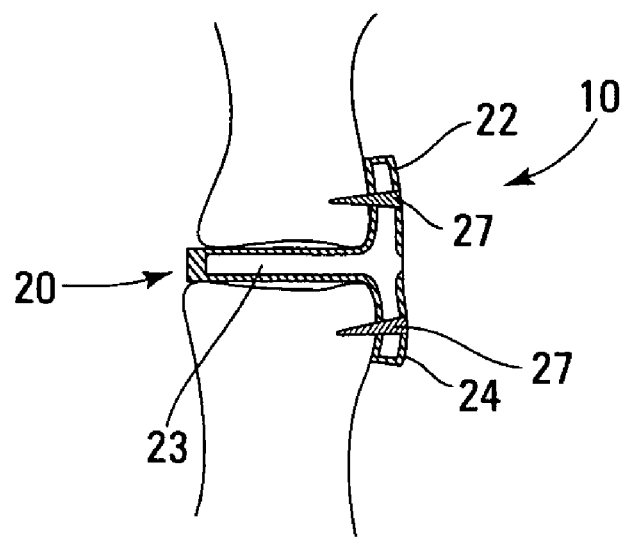
FIG. 7A shows an implant according to another embodiment of the present invention in a collapsed configuration.
Figure 7B:
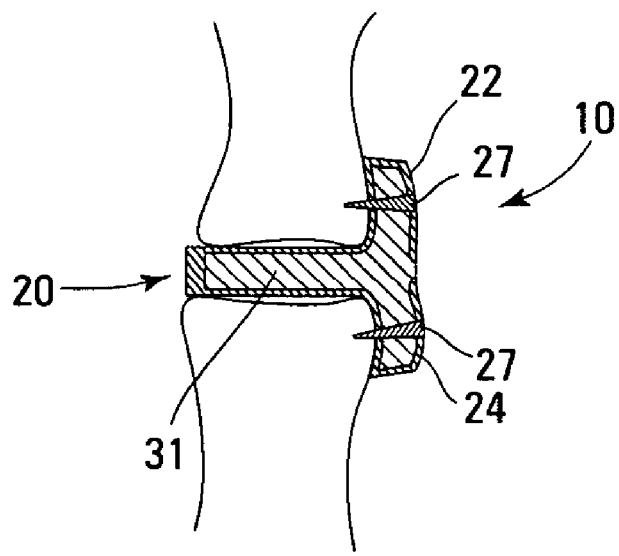
FIG. 7B shows the implant of FIG. 7A in an expanded configuration.

In one embodiment, as shown in FIGS. 7A and 7B, a sufficient amount of filler material 29 is injected into the cavity 23 to cause the bearing body 20 to conform to the profile of the facet surfaces adjacent the surfaces 21. In this manner, support offered by the facet bearing body 20 is distributed more evenly over the facet surfaces. It may not be necessary to resection or resurface the facet surfaces to provide a surface profile conforming to the shape of the implant. Thus, a single or generic implant 10 may be implanted into vertebral spaces under a variety of conditions.

The shape of the facet bearing body 20 and/or the cavity 23 may be chosen to provide expansion or extension after injection of material into the cavity 23 parallel to or at an angle relative to a longitudinal axis of the spine. For example, as shown in FIG. 3, the cavity 23 may be wedge-shaped so as to have a greater vertical height in a posterior region than in an anterior region. When filler material 29 is injected into the cavity 23, the implant 10 will tend to expand more greatly in the posterior region than in the anterior region. Implant 10 may thus be employed to realign the vertebrae relative to one another or to correct curvatures or anomalies of the spine.

In other embodiments, the filler material 29 may be injected into the cavity 23 prior to affixing the wings 22 and 24 to the vertebrae. This may help to prevent undue stress on the wings 22 and 24 and/or on the vertebrae caused by expansion of the implant 10.

After a chosen amount of material has been injected into the cavity 23, the injection tool is withdrawn and the opening 25 may be sealed. Finally, the material is allowed to cure or harden, causing the implant 10 to retain a chosen shape and volume.

An implant 10 according to the present invention may be used alone or in combination with other spinal surgical systems, including a total disc replacement.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An implant for use between the opposing facets of a facet joint between two adjacent vertebrae, comprising:
   an implant member including a facet bearing body, the facet bearing body having a cavity for receiving a filler material, the facet bearing body being wedge-shaped with a greater dimension at a second end than a first end; and
   at least one fixation wing extending from the first end of the facet bearing body for securing the implant to at least one of the two vertebrae, wherein the facet bearing body is positionable between the opposing facets of the facet joint and the at least one fixation wing is fixable to at least one of the two vertebrae and the cavity extends into the at least one fixation wing, wherein the implant is made of an elastomeric material.

2. The implant of claim 1 further comprising at least one bone engaging fastener for securing the at least one fixation wing to a vertebrae.

3. The implant of claim 2 comprising first and second bone engaging fasteners and first and second fixation wings, wherein the first and second fixation wings are each structured to be fixable to a lamina of a vertebra, wherein the first bone engaging fastener is structured to fix the first fixation wing to a lamina of one vertebra and the second bone engaging fastener is structured to fix the second fixation wing to a pedicle of the second vertebra.

4. The implant of claim 1 further comprising an opening in the facet bearing body to the cavity.

5. The implant of claim 4 wherein the opening is sealable.

6. The implant of claim 1 wherein the facet bearing body has a first vertical height when the cavity is empty and a second vertical height when the cavity is filled with the filler material.

7. The implant of claim 1 wherein the facet bearing body is a balloon having shape restricted characteristics.

8. The implant of claim 1 further comprising a filler material, wherein the filler material is an in situ curable polymer.

9. The implant of claim 1 further comprising a filler material, wherein the filler material is one of bone cement, polyurethane or elastomer.

10. The implant of claim 1 further comprising a filler material, wherein the filler material is curable from a fluid state to a hardened state.

11. A facet bearing implant for use between the opposing facets of a facet joint between two adjacent vertebrae, comprising:
- a balloon having shape restricted characteristics and a cavity, the balloon being wedge-shaped with a greater dimension at a second end than a first end;
- a filler material injectable into the cavity; and
- at least one fixation wing disposed at the first end of the balloon for securing the balloon to at least one of the two vertebrae, wherein the balloon is positionable between the opposing facets of the facet joint and the at least one fixation wing is fixable to at least one of the two vertebrae and the cavity extends into the at least one fixation wing, wherein at least a portion of the implant is made of an elastomeric material.

12. The facet bearing implant of claim 11 further comprising at least one bone engaging fastener for securing the at least one fixation wing to a vertebrae.

13. The implant of claim 12 comprising first and second bone engaging fasteners and first and second fixation wings, wherein the first and second fixation wings are each structured to be fixable to a lam ma of a vertebra, wherein the first bone engaging fastener is structured to fix the first fixation wing to a lamina of one vertebra and the second bone engaging fastener is structured to fix the second fixation wing to a pedicle of the second vertebra.

14. The facet bearing implant of claim 11 further comprising an opening in the balloon.

15. The facet bearing implant of claim 14 wherein the opening is sealable.

16. The facet bearing implant of claim 11 wherein the balloon is expandable from a first configuration to a second configuration upon injection of the filler material into the balloon.

17. The facet bearing implant of claim 16 wherein the balloon has at least one non-compliant region.

18. The facet bearing implant of claim 17 wherein the elastomeric portion and non-compliant region are configured such that in the second configuration the balloon has a predicted shape.

19. The facet bearing implant of claim 11 wherein the filler material is an in situ curable polymer.

20. The facet bearing implant of claim 11 wherein the filler material is one of bone cement, polyurethane or elastomer.

* * * * *

UNITED STATES PATENT AND TRADEMARK OFFICE
CERTIFICATE OF CORRECTION

| | | |
|---|---|---|
| PATENT NO. | : 7,744,630 B2 | Page 1 of 1 |
| APPLICATION NO. | : 11/274385 | |
| DATED | : June 29, 2010 | |
| INVENTOR(S) | : Mike E. Lancial | |

It is certified that error appears in the above-identified patent and that said Letters Patent is hereby corrected as shown below:

Column 10
Line 4 delete "lam ma", and insert therefor -- lamina --.

Signed and Sealed this
Twenty-first Day of June, 2011

David J. Kappos
*Director of the United States Patent and Trademark Office*